US008724864B2

(12) United States Patent
Persson et al.

(10) Patent No.: US 8,724,864 B2
(45) Date of Patent: May 13, 2014

(54) SYSTEM AND METHOD RELATING TO EXAMINATION OF AN OBJECT

(75) Inventors: Mikael Persson, Alingsas (SE); Andreas Fhager, Gothenburg (SE); Parham Hashemzadeh, Gothenburg (SE)

(73) Assignee: Medfield Diagnostics AB, Gothenburg (SE)

( * ) Notice: Subject to any disclaimer, the term of this patent is extended or adjusted under 35 U.S.C. 154(b) by 1065 days.

(21) Appl. No.: 12/302,055

(22) PCT Filed: May 22, 2007
(Under 37 CFR 1.47)

(86) PCT No.: PCT/SE2007/000500
§ 371 (c)(1),
(2), (4) Date: Sep. 3, 2009

(87) PCT Pub. No.: WO2007/136334
PCT Pub. Date: Nov. 29, 2007

(65) Prior Publication Data
US 2010/0067770 A1    Mar. 18, 2010

Related U.S. Application Data

(60) Provisional application No. 60/747,838, filed on May 22, 2006.

(51) Int. Cl.
*G06K 9/00* (2006.01)

(52) U.S. Cl.
USPC .......................................................... 382/128

(58) Field of Classification Search
USPC .................... 382/128; 600/407, 430; 607/101
See application file for complete search history.

(56) References Cited

U.S. PATENT DOCUMENTS

| 5,807,257 | A | 9/1998 | Bridges |
| 6,061,589 | A | 5/2000 | Bridges et al. |
| 6,330,479 | B1* | 12/2001 | Stauffer ........................ 607/101 |
| 2004/0077943 | A1 | 4/2004 | Meaney et al. |
| 2006/0058606 | A1* | 3/2006 | Davis et al. .................... 600/407 |
| 2006/0084859 | A1 | 4/2006 | Johnson et al. |
| 2006/0241410 | A1* | 10/2006 | Fang et al. .................... 600/430 |

FOREIGN PATENT DOCUMENTS

JP    2007061359 A    3/2007

OTHER PUBLICATIONS

"Introduction to Plasma Physics"; I.H. Hutchinson; 2001; Chapter 5 "Electromagnetic Waves in Plasmas".*
Miyakawa et al: "An Attempt of Time Domain Microwave Computed Tomography for Biomedical Use", Conf. Proc. 23rd EMBS International Conference, Oct. 25-28, 2001, pp. 3300-3303, Istanbul, Turkey.

(Continued)

Primary Examiner — John Pauls
(74) Attorney, Agent, or Firm — Young & Thompson

(57) ABSTRACT

The present invention relates to a system and method for non-invasively examination of internal structures of an object by producing dielectric images utilizing reflection and transmission 5 measurements using microwave radiation, characterized by an antenna array surrounding a region of interest for the examination, a microwave transceiver for measuring reflected and transmitted electromagnetic fields, a computational module for receiving detected radiation and for processing data based on the detected radiation, the computational module further being operatively arranged to execute a reconstruction procedure utilized to compute an image of the 10 dielectric profile under detection.

22 Claims, 7 Drawing Sheets

(56) References Cited

OTHER PUBLICATIONS

Xu et al: "Microwave Imaging via Space-Time Beamforming: Experimental Investigation of Tumor Detection in Multilayer Breast Phantoms", Aug. 2004, IEEE Transactions on Microwave Theory and Techniques, vol. 52, No. 8, pp. 1856-1865.

Xu Li, et al., "Microwave Imaging via Space-Time Beamforming: Experimental Investigation of Tumor Detection in Multilayer Breast Phantoms", IEEE Transactions on Microwave Theory and Techniques, Aug. 2004, vol. 52, pp. 1856-1865.

M. Miyakawa et al., "An Attempt of Time Domain Microwave Computer Tomography for Biomedical Use", Proceedings of the 23rd Annual International Conference of the IEEE, vol. 4, pp. 3300-3303.

International Search Report dated Oct. 16, 2007, from corresponding PCT application.

* cited by examiner

SYSTEM AND METHOD RELATING TO EXAMINATION OF AN OBJECT

TECHNICAL FIELD OF THE INVENTION

The present invention relates to a system for non-invasively examination of internal structures of an object using microwave radiation.

BACKGROUND OF THE INVENTION

Breast cancer is a serious health problem for women worldwide. Worldwide breast cancer is the second most common form of cancer with about 1.15 million new cases diagnosed in the year 2002. A relatively favorable prognosis, compared to other cancer forms, resulted in about 410 000 deaths the same year, according to the cancer statistics published by D. M. Parkin, F. Bray, J. Ferlay and P. Pisani, entitled "Global cancer statistics, 2002" in *CA: A Cancer Journal for Clinicians*, vol. 55, pp. 74-108, March 2005. This figure motivates researchers all over the world in various fields of tumor detection, diagnostics and treatment. In the process of diagnosing malignant breast cancer imaging has come to play an important role. Especially X-ray mammography is used extensively even though it has some problems, mainly due to the contrast between the tumor and the surrounding tissue which could often be as low as a few percent. It is therefore of great interest to develop alternative or complimentary imaging techniques. These methods should preferably be relatively inexpensive, easy to use and they should produce images in real time.

The breast cancer treatment today is conducted on the basis that an early diagnosis, i.e. when the tumor is small, is crucial for successful treatment and is important for the long-term survival rate. Michaelson et al, "Predicting the Survival of Patients with Breast Carcinoma using Tumor Size," published in *Cancer*, vol. 95, pp. 713-723, August 2002, have performed a survival analysis and developed a formula for estimating the probability of survival based on the tumor size. Their investigations show that the chance of survival for breast cancer patients is directly related to the size of the tumor at the time of diagnosis.

In the process of diagnosing malignant breast cancer imaging has come to play an important role. Especially X-ray mammography is used extensively since it fulfils most of the requirements on a good imaging method. These requirements are that it should have a high specificity and sensitivity to malignant tumors, it should not take up large amounts of manpower or time and it should be non-invasive, harmless and cost efficient.

In many screening programs X-ray mammography has proved to reduce the breast cancer mortality and today it is the routine examination method for breast cancer imaging. It is well recognized and acknowledged for its ability to detect and characterize breast tumors. Unfortunately there are some important limitations, such as high false-positive detection rate. There are reports indicating a false-positive detection rate of 2.6-15.9%, i.e. that the mammogram shows a structure that are improperly interpreted as a tumor. The same publications also conclude that the variation is strongly dependent on the experience of the radiologist. There are also estimates that malignant tumors are found in 10-50% of the patients called back for breast biopsy based on the findings in the mammogram.

The false-negative rate is also significant and reported to be 4-34%, depending on the definition of a false-negative mammogram. Also here is has proven that the experience of the radiologist and the population selected for the study strongly influences the estimated percentage rate. In general it is considered that about 5-15% of the malignant breast cancers are not detected. An important contribution to these numbers comes from the difficulty in imaging radiographically dense breasts, containing a large amount of fibroglandular tissue. About 25% of all women, especially young women, have this type of breasts and other imaging methods than X-ray mammography plays a more important role here. One of the reasons for failure to detect some tumors with the X-ray mammographic technique can be attributed to the low contrast between the tumor and the surrounding tissue. This is especially evident in the radiographically dense breast, which contains large amounts of glandular and fibrous tissue, with similar X-ray attenuation as the lesion.

For the patient safety and comfort there are few additional drawbacks with X-ray mammography. Among patients it is sometimes seen as an uncomfortable and painful examination due to the need for breast compression. Exposing patients to ionizing radiation on a regular basis within mammography screening programs is also not entirely satisfactory. Even if the radiation dose is kept very low there is a risk that the repeated exposure to X-rays will induce carcinoma in the breast.

There exist complimentary imaging methods that avoid the ionizing radiation and the uncomfortable breast compression. The most important are ultra sound imaging and contrast-enhanced magnetic resonance imaging (MRI). None of these methods are suitable for or have been used in a mass screening program although they are in some cases useful later in the process of diagnosing malignant breast cancer, and for evaluating dense breasts. Other methods such as X-ray computed tomography, digital subtraction angiography, diaphanography and imaging using radio nuclides only has a small role in breast cancer examination today.

SHORT DESCRIPTION OF THE INVENTION

Following the above discussion one can conclude that there is a scope to develop complementing and/or alternative imaging methods. Due to reports about advantageous dielectric properties of the breast compared to the properties of malignant tissue at microwave frequencies it has been proposed that microwave imaging would be a promising method. The method is currently under increasing interest and it has the potential of fulfilling many of the criteria characterizing a good imaging method. Ionizing radiation is avoided as is the uncomfortable breast compression. Due to the relatively large dielectric contrast, at microwave frequencies, between tumors and healthy tissue it has the potential to be both sensitive and specific to small tumors. It would also not be as expensive as magnetic resonance imaging and the examination is expected to be very fast.

SHORT DESCRIPTION OF THE DRAWINGS

In the following the invention is described with reference to a number of exemplary embodiments, illustrated schematically in the attached drawings, in which:

FIG. 1 is a schematic sketch of the microwave tomography system according to the present invention, FIG. 2 is a schematic sketch of a carrier structure according to the present invention, FIG. 3 is a schematic sketch of the entire imaging system and its major components, FIG. 4 shows measured permittivity values for healthy breast tissue (bottom) and tumor tissue (middle), FIG. 5 shows measured conductivity values for healthy breast tissue (bottom) and tumor tissue (middle), FIG. 6 shows a reconstruction of two tumors in the breast with the reconstruction method according to present invention. The original object can be seen in FIG. 8.

DESCRIPTION OF THE INVENTION

The objective of this invention is to provide a system for imaging of female breasts but also other types of biological tissues. The system will generate images if the internal dielectric properties of the tissue. The dielectric properties of interest are the permittivity and the conductivity of the tissue, determined at the frequencies corresponding to the spectral content of the microwave radiation used for the imaging procedure. Transmission and reflection measurements, where the transmitters/receivers are placed on a boundary entirely or partly surrounding the target, are used in a computational method to recover the internal dielectric properties of the breast. The microwave radiation measurements are broadband and frequencies in the range from around 100 MHz to about 3 GHz or above can be utilized.

One aspect of this invention concerns a measurement system where the microwave radiation used for the imaging is transmitted and after scattering by and inside the tissue under investigation again detected by microwave receivers. The fundamental idea with this innovation is that microwave scattering measurements are made at a large number of frequencies and that the full dielectric tensor is reconstructed by measuring and processing in the image reconstruction method cross polarization components of the radiation. The system 100, illustrated in FIG. 1, consists of three major components, the antenna system 110, the microwave transmitting/receiving unit 120 and the data processing unit 130. In this figure an example of the antenna array is shown configured as a circular array of monopoles. Other types of antennas and other array configurations could also be used and are included in the present invention. In case of performing cross polarization measurements with monopoles it is also necessary that the antennas can receive horizontally polarized field components. One possible solution to this is to mount horizontally aligned monopoles antennas beside the vertically aligned monopoles. Cross mounted dipoles could for instance also be used or different types of patch antennas. The microwave transmission/receiving hardware is designed to measure a large number of frequency components in the frequency range of interest. The number of components could be in the range from one up to several thousand.

For the measurements the antenna array is mounted below a hole in a bed such that the patient can be positioned prone with the breast pendant inside the antenna array and measurements can be made where the microwave radiation is transmitted into the tissue and the scattered radiation can be picked up by the receivers. For improved coupling of the electromagnetic radiation into the body part it is necessary to use a coupling fluid. This means that the antennas are mounted in a tank for the fluid and that the breast is positioned pendant in the fluid.

Figure 2:
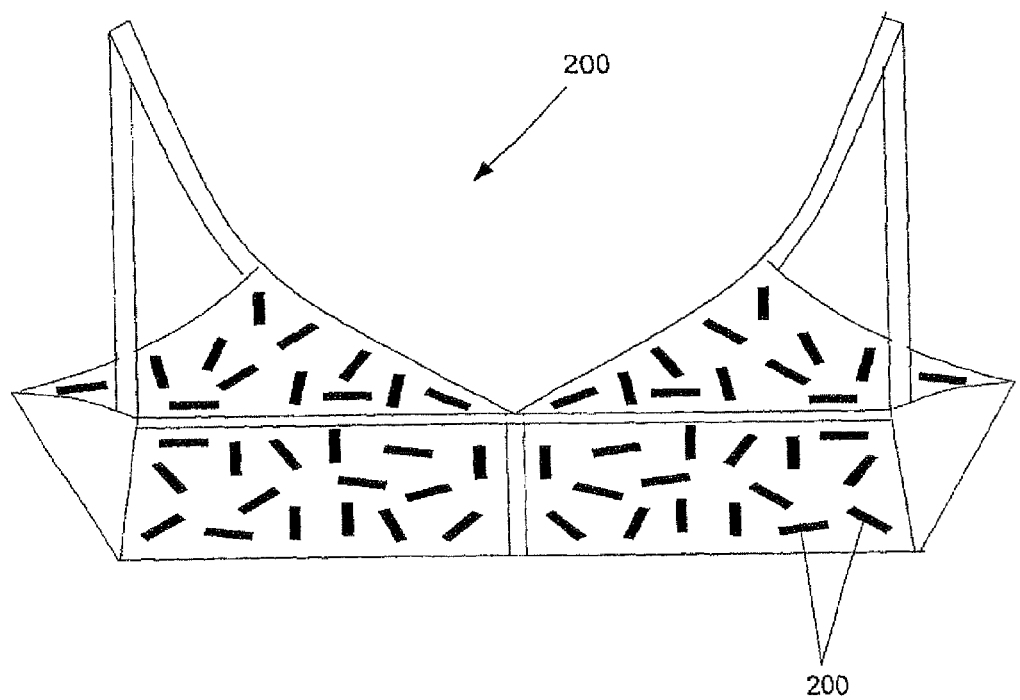

Another aspect of this invention concerns a specialized configuration and design of the antenna system utilized for the transmission/reflection measurements of, e.g. the breast. This is a new design of the antennas system that will optimize the comfort for the patient at the time of examination. In this design the antennas are mounted in the fabric of a dedicated bra designed to hold and support the antennas. The principal design of such a bra is sketched in FIG. 2, which is a schematic sketch of a carrier structure 200, formed as a bra for breast examination, with the antennas 210 mounted inside the bra. The bra is seen from behind and the black squares represent the antennas 210. The antennas could be dipoles, patch antennas or any other type of antennas. Other garments can also be used for supporting the antennas, when other body parts are examined.

Figure 3:
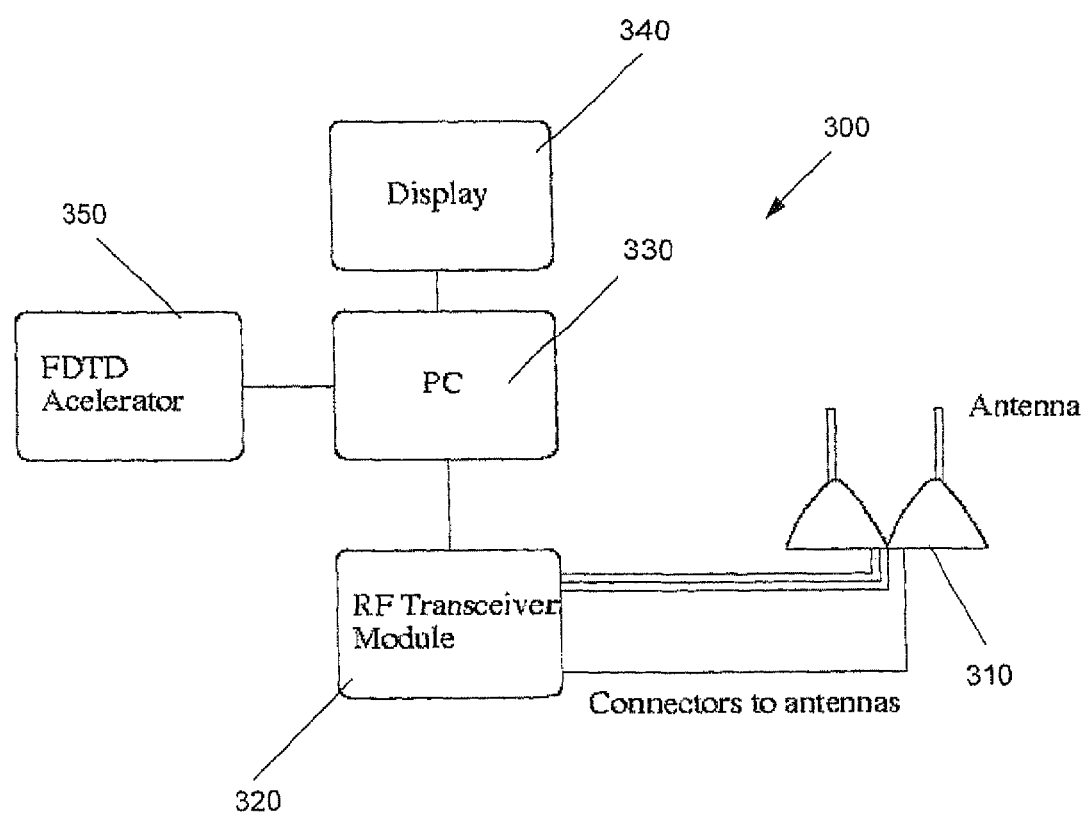

The antennas could be arbitrarily oriented with respect to each other. At the examination the patient would simply wear the bra while the measurements are made. With this antenna configuration a number of antennas are surrounding the breasts and their exact position and orientation has to be known or otherwise determined before the image of the internal dielectric properties can be recovered. The antennas could for instance be flexible patch antennas on a substrate that readily can be attached inside, in the fabric or outside the bra. Other examples of alternatives that could be used are dipole antennas or dielectrically loaded horn antennas. However the present antenna system is not limited to using a bra for breast imaging but an arbitrary garment could be used for imaging or hyperthermia treatment of any body part. For the image reconstruction method where the antenna system has to be accurately modeled it is necessary to know the position and orientation of each individual antenna. This information could for instance be obtained by broadband microwave transmission measurements between neighboring antennas. One method to accomplish this is the POCS method, for example described by A. Hero and D. Blatt, "Sensor network source localization via projection onto convex sets (POCS)," in proceedings of *IEEE International Conference on Acoustics, Speech and Signal Processing*, 2005, Philadelphia, 2005, or the APOCS methods described by D. Blatt and A. Hero, "APOCS: A rapidly convergent source localization method for sensor networks," in proceedings of *IEEE Workshop on Statistical Signal Processing*, Bordeaux, 2005. To obtain sufficiently high accuracy in the positioning it is also necessary to use a number of external antennas serving as reference antennas. The positions of these antennas have to be determined and verified by independent measurements such that the antennas inside the bra can be positioned with respect to these external antennas. An alternative to using a flexible antenna array where the individual antennas can move in comparison to each other is to use a fixed bra with the antennas mounted in fixed positions. In that way the antenna positions and orientation will remain constant and thus it is sufficient to determine the positions of the antennas when the antenna array is manufactured once and for all. To accommodate all individual patients, with breast that can vary vastly in size from patient to patient, it will instead be necessary to use several differently sized bras. Another advantage of this bra is that is will provide a light fixation of the breast during the measurements, thereby reducing the effect of movement artifacts. The antenna system is further supported with equipment to conduct and control the measurements and a data processing unit containing computational hardware used for executing the image reconstruction method. The major components of such a system 300 design are shown in FIG. 3, comprising antenna array 310, an RF transceiver module 320, a computer unit 330, display 340 and FDTD accelerator 350.

Figure 1:
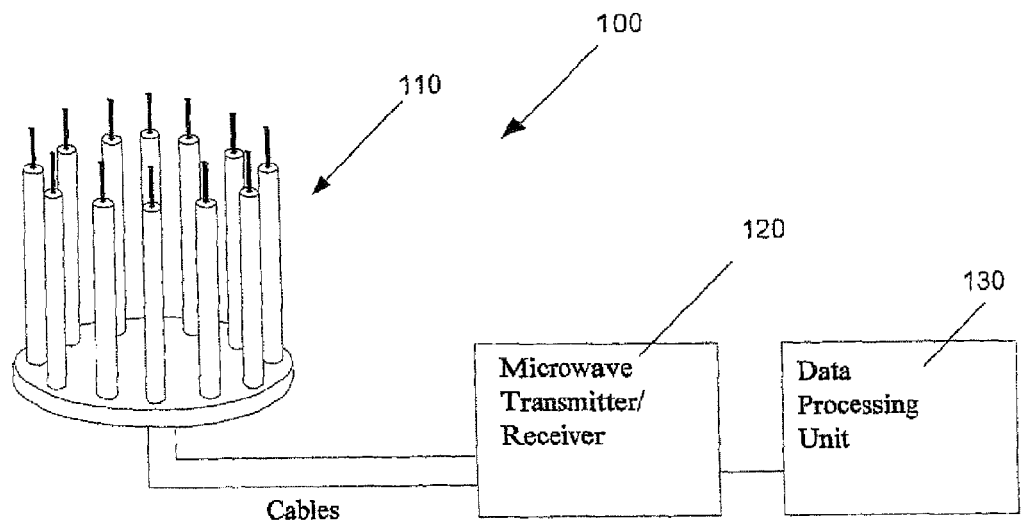

The antenna array is connected to the microwave transceiver module which is transmitting/receiving the electromagnetic radiation to/from the antennas. With this equipment measurements are conducted at single frequencies, one at a time over the desired frequency span. A PC (computer unit) is used to control the microwave measurements, reconstruct the image and to display the results. The antenna bra could as well be replaced by an antenna system as shown in FIG. 1.

Another aspect of this invention concerns the image reconstruction method, which based on the measurements mathematically reconstructs the dielectric properties of the internal breast tissue. The measurements in this application are, as already mentioned, made over a large frequency band, which could range from 100 MHz to 3 GHz or more with measurements at several hundred or up to several thousand individual frequencies. The reason is that more frequency components in the measurements could contribute to more accurate reconstructions compared to when using only one or a few frequency components. This in turn could make the identification of different internal structures inside the breast more accurate and consequently the diagnosis of possible tumors could be made more accurately. In the image reconstruction software a computational model based on a time-domain solver for Maxwell's equations are utilized, in our case the FDTD model but other models such as FEM or MOM could be used. Thus the measurement data obtained at several individual frequencies have to be converted from frequency-domain to time-domain via a Fourier transformation. When pulses have been synthesized from the measurement data comparison of the computational model of the imaging system can be made and the difference between the signals can be used to update the reconstruction. Mathematically this is made by defining a cost functional containing the difference between the measured and the computed signals. The update of the dielectric properties, made in each iteration of the method, is determined by differentiating the cost functional with respect to the permittivity and conductivity. In this way the reconstruction of the internal dielectric properties can successively be refined giving better and better images. A description of this reconstruction method can be found for example in the following publications:

M. Gustafsson and S. He, "An optimization approach to two-dimensional time domain electromagnetic inverse problems," *Radio Sci.*, vol. 35, pp. 525-536, 2000.

T. Tanaka, T. Takenaka, and S. He, "An FDTD approach to the time-domain inverse scattering problem for an inhomogeneous cylindrical object," *Microwave Opt. Technol. Lett.*, vol. 20, pp. 72-77, 1999.

I. T. Rekanos, "Time-domain inverse scattering using Lagrange multipliers: an iterative fdtd-based optimization technique," *Journal of Electromagn. Waves and Appl.*, vol. 17, pp. 271-289, 2003.

A. Fhager and M. Persson, "Comparison of two image reconstruction methods for microwave tomography," *Radio Science*, vol. 40, Art. No. RS3017, June, 2005.

Figure 9:
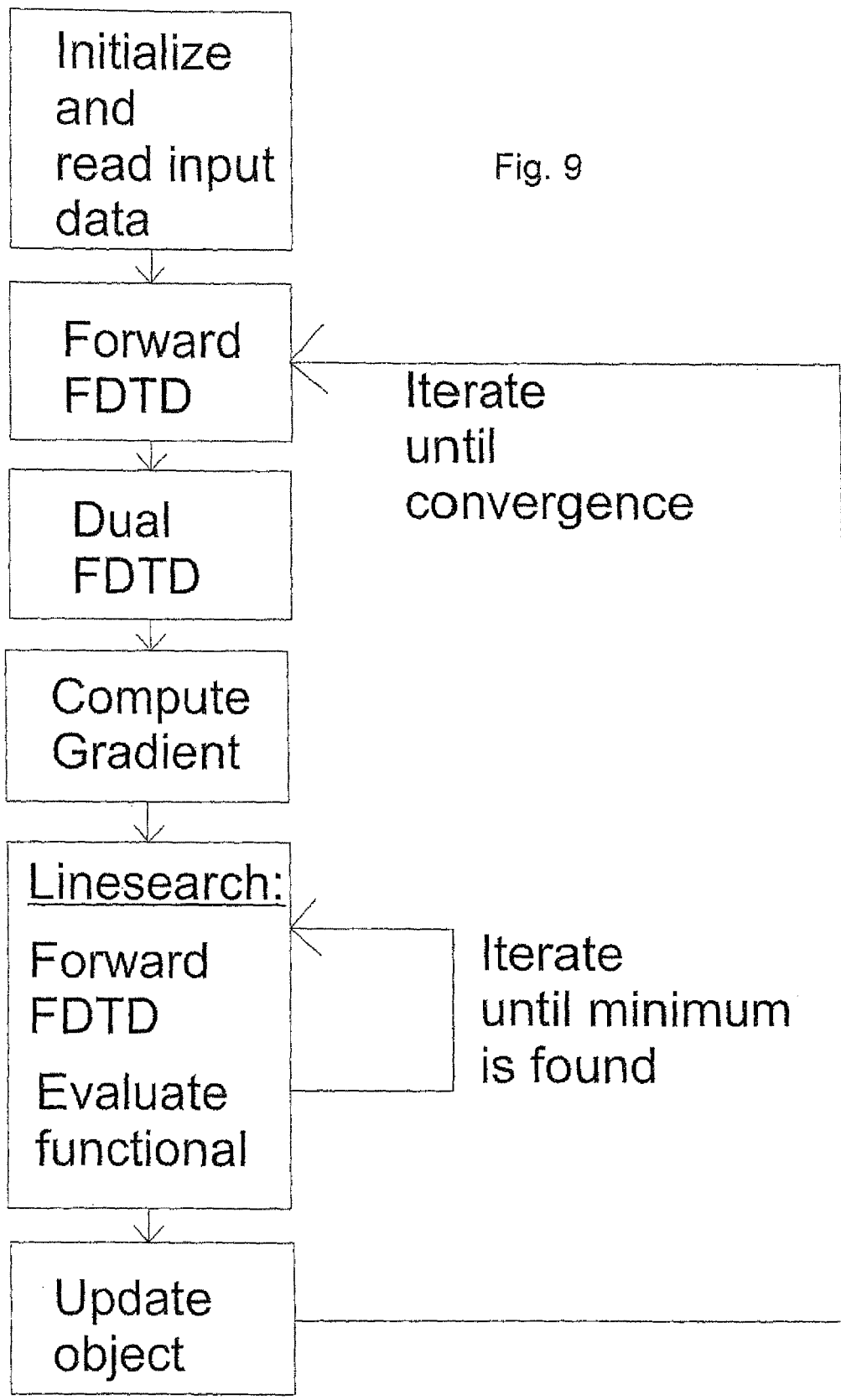
FIG. 9 is a flow diagram over a method according to the present invention.

One example of the method is illustrated in FIG. 9, and shortly comprises the steps of:

1. Measurement data is read and the computation is initialized.
2. Forward FDTD simulations of the systems are made.
3. Dual FDTD simulations are made. The driving source in this problem is the residual between the forward FDTD simulation and the corresponding measurements.
4. Gradients are computed from the forward and the dual FDTD simulations.
5. A line search in the negative direction of the gradient is made. The line search involves several FDTD simulations where the functional is evaluated and bases on these evaluations the minimum point is estimated.
6. The object is updated and the process is started over from step 2. This procedure is iterated until the reconstruction process has converged.

Based on experience with this method it can be seen that when reconstructing an object it starts by appearing in the first iterations as an object having a significantly larger diameter and lower dielectric properties than when comparing to the true dielectric values, differs only little from the background values. In the following iterations the dielectric values of the object slowly approaches the true values at the same time as the size is decreasing towards the correct value. When simultaneously imaging objects with different size but with identical dielectric properties a tendency towards the smaller objects ending up in the reconstructed image as having lower dielectric values than the larger objects has been noticed. It is not possible to resolve objects smaller than a certain portion of the wavelength corresponding to the center frequency of the electromagnetic pulse. In that case, if at all appearing in the reconstruction, the objects will usually have too large size with dielectric properties that has not yet converged to the true values of the original objects. The invention constitutes a method to resolve the above problems, to speed up the reconstructions and to enable resolving smaller objects using a given center frequency in the pulse it is proposed utilization of a priori knowledge of the dielectric properties of the breast cancer tumors. This approach can be justified based on dielectric measurements of cancerous tissue found in several independent publications where quite a unanimous picture of the dielectric properties is given in the frequency range of interest:

S. S. Chaudhary, R. K. Misha, A. Swarup and J. M. Thomas, "Dielectric Properties of Normal & Malignant Human Breast tissue at Radiowave and Microwave Frequencies," *Indian J. Biochem. Biophys.*, vol. 21, pp. 76-79, February 1984.

A. J, Surowiec, S. S. Stuchly, J. R. Barr, A. Swarup, "Dielectric Properties of Breast Carcinoma and the Surrounding Tissues," i IEEE Trans. Biomed. Eng., vol. 35, pp. 257-263, April 1988.

W. T. Joines, Y. Zhang, C. Li and R. L. Jirtle, "The measured electrical properties of normal and malignant human tissues from 50 to 900 MHz," *Med. Phys.*, vol. 21, pp. 547-550, April 1994.

A. M. Campbell and D. V. Land, "Dielectric properties of female human breast tissue measured in vitro at 3.2 GHz," *Phys. Med. Biol.*, vol. 37, pp. 193-210, 1992.

D.-S. Yoo, "The dielectric properties of cancerous tissues in a nude mouse xenograft model," *Bioelectromagnetics*, vol. 25, pp. 492-497, 2004.

W. T. Joines, "Frequency-Dependent Absorption of Electromagnetic Energy in Biological Tissue," *IEEE Trans. Biomed. Eng.*, vol. 31, pp. 17-20, January 1984.

P. M. Meaney, M. W. Fanning, D. Li, S. P. Poplack and K. D. Paulsen, "A Clinical Prototype for Active Microwave Imaging of the Breast," *IEEE Trans. Microwave Theory Tech.*, vol. 48, pp. 1841-1853, November 2000.

C. Gabriel, S. Gabriel and E. Corthout, "The dielectric properties of biological tissues: I. Literature survey," *Phys. Med. Biol.*, vol. 41, pp. 2231-2249, 1996.

S. Gabriel, R. W. Lau and C. Gabriel, "The dielectric properties of biological tissues: II. Measurements in the frequency range 10 Hz to 20 GHz," *Phys. Med. Biol.*, vol. 41, pp. 2251-2259, 1996.

S. Gabriel, R. W. Lau and C. Gabriel, The dielectric properties of biological tissues; III. Parametric models for the dielectric spectrum of tissues," *Phys. Med. Biol.*, vol. 41, pp. 2271-2293, 1996.

Figure 4:
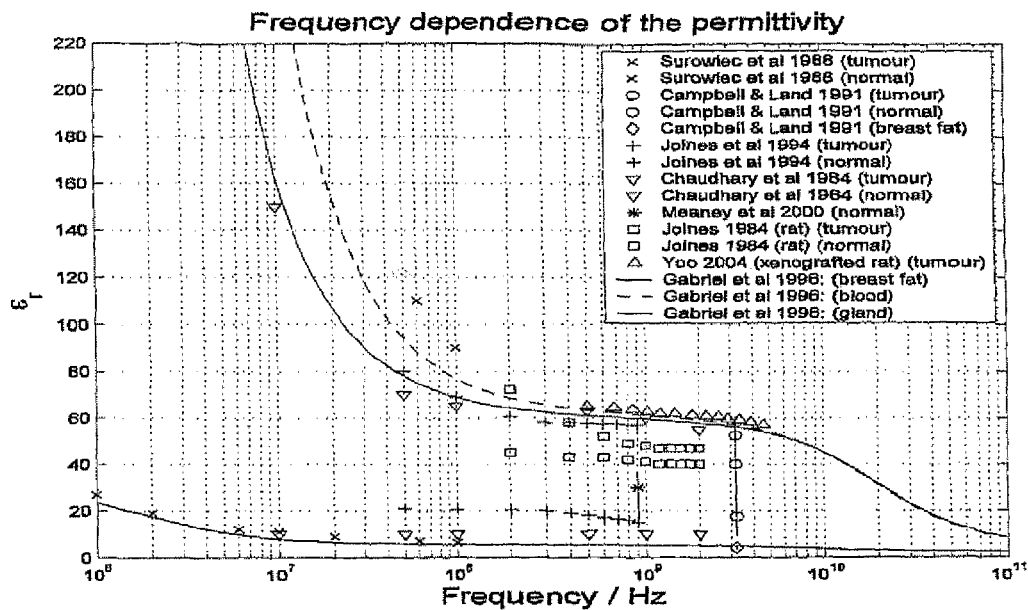
Figure 5:
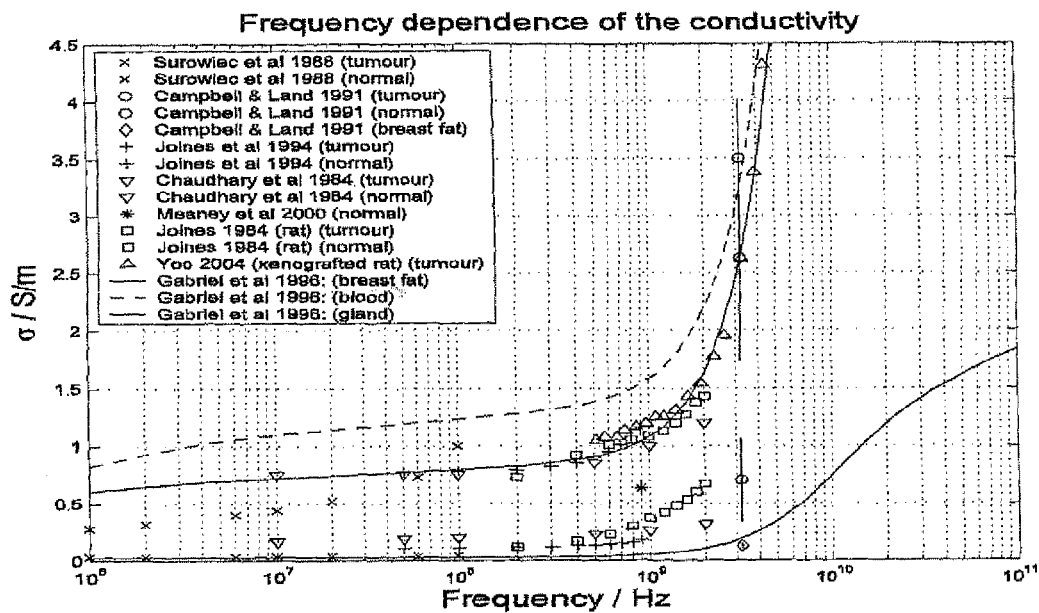
Figure 6:
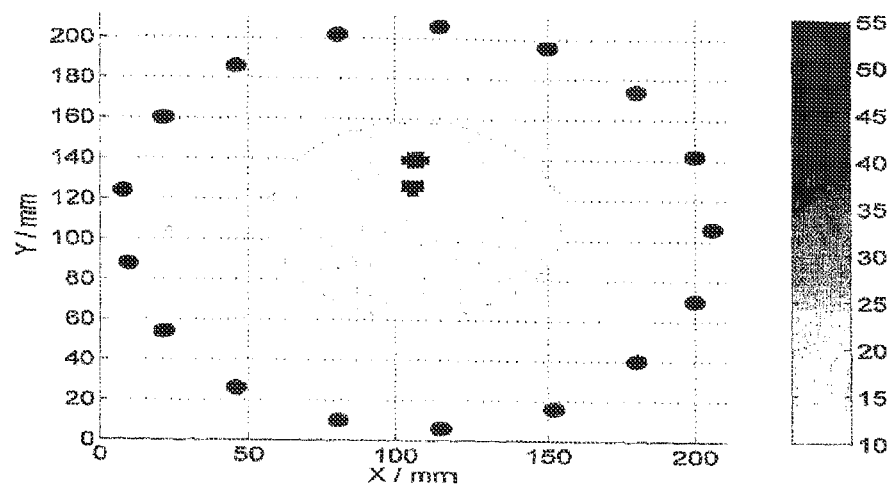
Figure 7:
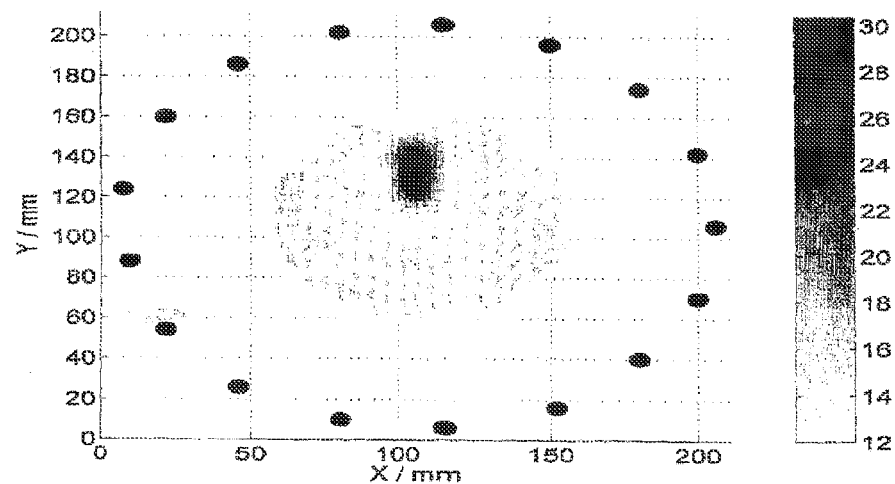
FIG. 7 shows a reconstruction of the same case as FIG. 6 but using a conventional reconstruction method. The original object can be seen in FIG. 8.
Figure 8:
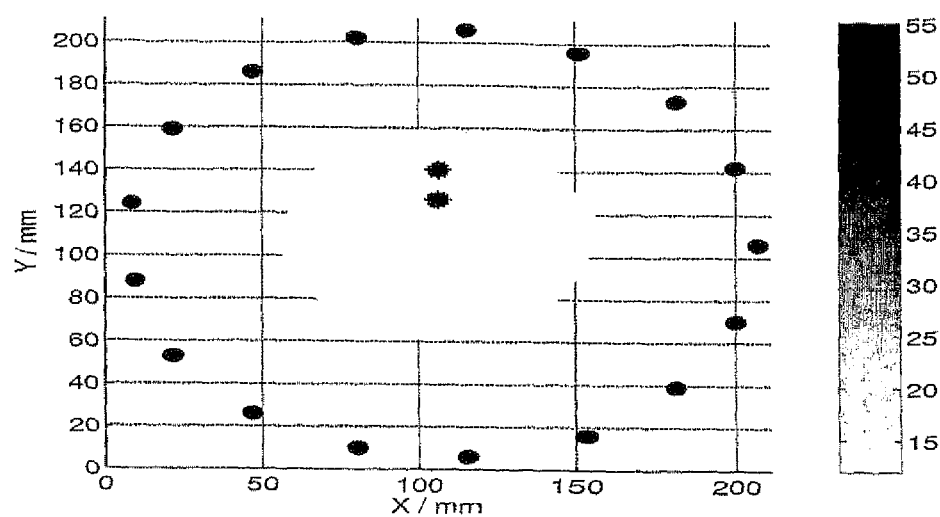
FIG. 8 shows the original object used to demonstrate the resolving capabilities of the new reconstruction method.

A compilation of the results regarding dielectric data for the tumor tissue and the healthy breast tissue can be found in FIGS. 4 and 5. To perform the reconstructions the method can be described in the following way: First the reconstruction is made according to the method described by for example [Gustafsson et al, 2000], [Tanaka et al, 1999], [Rekanos et al, 2003] and [Fhager et al, 2005]. In the extension of the method, which is a part of the present invention, this step of the reconstruction is made with frequency content of the electromagnetic pulse and smoothing of the reconstructed image such that only the overall structure, size and properties of the breast is obtained. In the proceeding iterations of the reconstruction procedure the frequency content of the pulse is increased, to enable an improved resolution. The gradients are now computed in the same way as before but after that our new invention regarding the reconstruction is effectuated. A threshold level is determined in the gradient and all points in space where the gradient value is above the threshold value are assigned the a priori dielectric values. The threshold level is determined such that the cost functional is minimized. In the following iterations the gradients are now used to update the shape, size and location of the object(s). It is also checked for if any new objects can be found. The a priori values are not limited to one fixed number in conductivity and permittivity but could also be a range within which the reconstructed values can be found. In FIG. 6 a reconstruction with this technique is shown and compared to a reconstruction using the conventional technique, shown in FIG. 7. The same frequency content was used in the both reconstructions. A significant increase in the resolving ability can be seen. In FIG. 8 the original object is shown. It would however have been possible to resolve the object in FIG. 7 with the conventional method but in that case the frequency of the illuminating field would have to be significantly increased. The invention thus allows the reconstruction to be made with lower frequencies, thus reducing the demands on the measurement equipment.

Figure 10:
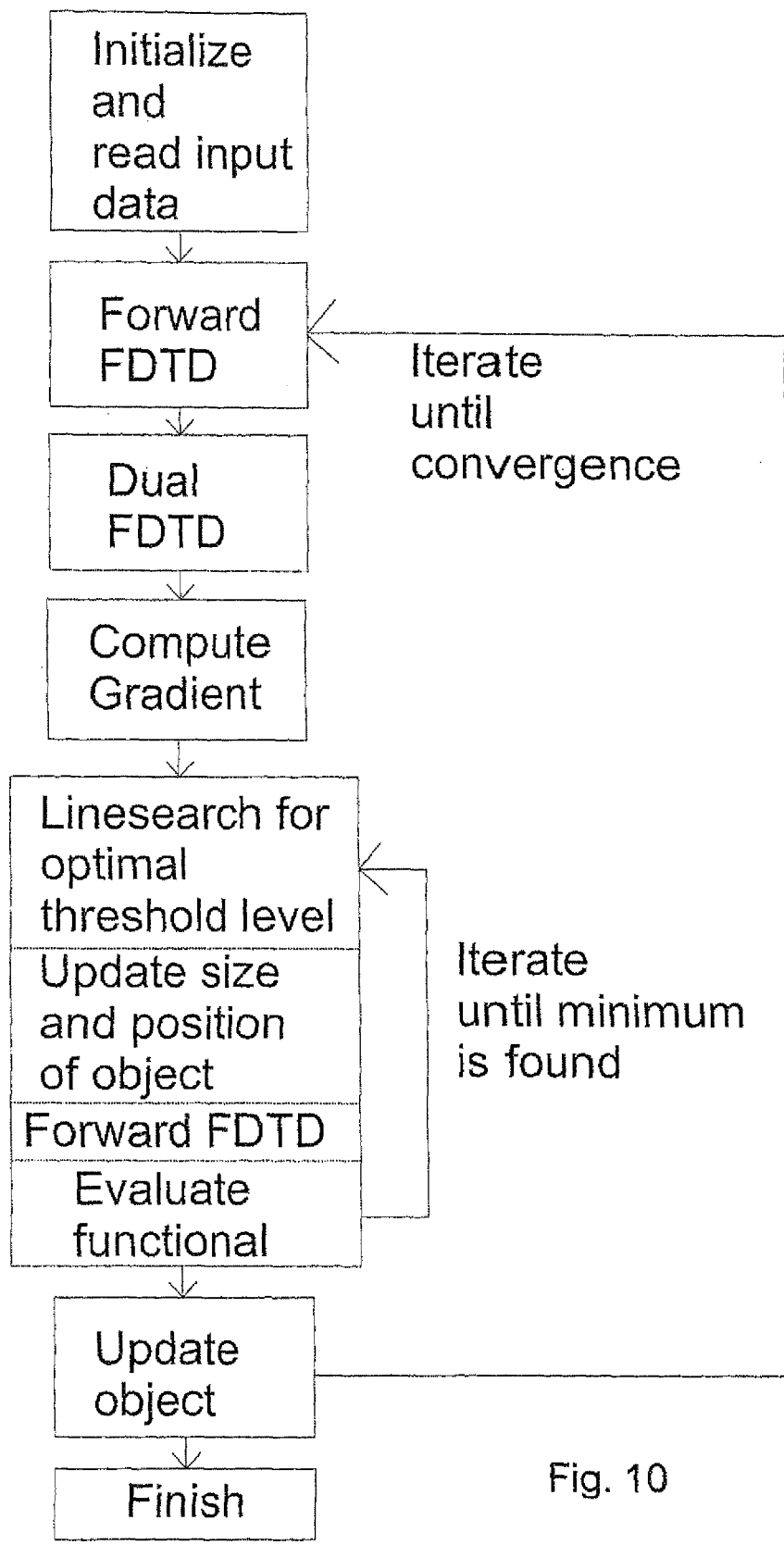
FIG. 10 is a flow diagram over a method according to the present invention.

FIG. 10 illustrates the steps of the extended method:
1. Measurement data is read and the computation is initialized
2. Forward FDTD simulations of the systems are made.
3. Dual FDTD simulations are made. The driving source in this problem is the residual between the forward FDTD simulation and the corresponding measurements.
4. Gradients are computed from the forward and the dual FDTD simulations.
5. A line search is made where the location of a threshold level in the gradient is optimized. In that everything that is above the threshold level is associated with the object and everything below is given the background material properties. In this process new objects will be located. In the next step the same gradients as computed in step 4 are used in a search process to see if the already found objects are located in the correct position or if they should be moved. Also here the line search involves several FDTD simulations where the functional is evaluated and bases on these evaluations the minimum point is estimated. In comparison to the original method the difference is in over which parameters the line search is made and thus how the objects are found and located. This extended method allows for including a priori object data in the reconstruction procedure.
6. The object is updated and the process is started over from step 2. This procedure is iterated until the reconstruction process has converged.

Yet another aspect of the invention regards the fact that the breast tissue does not exhibit isotropic dielectric properties, instead different tissues show different levels of anisotropy. For instance fat could be expected to have quite low isotropic properties since there are no directional structures in the tissue. Ducts or fibers, for example, which are elongated objects, will on the other hand show fairly strong anisotropic properties. Other tissues such as skin, glands, blood vessels, tumors etc, will all have different anisotropic behavior that, together with the reconstructed values of the permittivity and conductivity constitute the parameters defining the tissue. When characterizing the different tissue types inside the breast, and distinguishing tumors from glands and other blood rich organs this kind of information is important in order to make an accurate diagnosis. A measure of the anisotropy is giving such important information about the directional behavior of the tissue. The previously described reconstruction method is able to determine the dielectric parameters modeled as an isotropic constant according to the constitutive relations, D=∈E, J=σE. In the anisotropic model these relations are extended to matrix relations where each of the field components are related according to $$\begin{bmatrix} D_x \\ D_y \\ D_z \end{bmatrix} = \begin{bmatrix} \varepsilon_{11} & \varepsilon_{12} & \varepsilon_{13} \\ \varepsilon_{21} & \varepsilon_{22} & \varepsilon_{22} \\ \varepsilon_{31} & \varepsilon_{32} & \varepsilon_{33} \end{bmatrix} \begin{bmatrix} E_x \\ E_y \\ E_z \end{bmatrix}, \quad \text{Eq. (1)}$$

$$\begin{bmatrix} J_x \\ J_y \\ J_z \end{bmatrix} = \begin{bmatrix} \sigma_{11} & \sigma_{12} & \sigma_{13} \\ \sigma_{21} & \sigma_{22} & \sigma_{22} \\ \sigma_{31} & \sigma_{32} & \sigma_{33} \end{bmatrix} \begin{bmatrix} E_x \\ E_y \\ E_z \end{bmatrix}. \quad \text{EQ. (2)}$$

Most real tissue is reciprocal implying that the tensors in Eq. (1) and (2) are symmetric. To be able to perform the reconstruction of the full tensor it is necessary to make transmission/reflection measurements of aligned polarization directions on the transmitter and the receiver together with measurements of cross polarization radiation. The invention here is describing a method to fully reconstruct the dielectric tensors according to Eq. (1) and (2) above. This is particularly well suited for the antenna configuration in the bra where the antennas can be positioned in a three dimensional space, arbitrarily oriented. After the measurements have been conducted and the dielectric parameters have been reconstructed a diagonalization of the tensors are made. This process will reveal the inherent directional structures of the tissue and this together with the numerical values of the permittivity and conductivity will enable the identification of the different tissues and it would be possible to detect and separate objects with a directional property, such as fibers, ducts etc., from uniform tissue masses, such as fat and tumors.

Another aspect of the invention regards the implementation of the computational hardware performing the electromagnetic modeling required in the reconstruction method. Computational wise the most demanding and time consuming task in the reconstruction method is the FDTD simulations. Today the reconstruction is usually made offline at PC computers or parallel computers. The required reconstruction time could be up to several hours. The present invention constitutes an important system design which could enable the manufacturing of an online reconstruction modality significantly speeding up the computations and allowing for real time reconstructions. The calculation of the gradients requires two simulations for each transmitter used; with 20 transmitters this means 40 independent simulations. After the gradients have been computed it is necessary to minimize the cost functional. This requires around ten independent evaluations of the functional. Each at a cost of as many simulations as there are transmitters; again with 20 transmitters this means 200 simulations. Further it requires about 10-30 iterations for the reconstruction of the image to converge; this means 2400-7200 independent FDTD simulations are required for the entire reconstruction process. For the medical imaging device it is crucial that images are produced in real time or at least in almost real time. Therefore it is of undisputed importance that the computations can be made as fast as possible. Since the FDTD simulations are the most time consuming part it is natural to look for ways to speed it up. The FDTD simulations for each transmitter are independent of each other and well suited for a parallel implementation. There exists custom made hardware implementing the FDTD method which can significantly speed up the simulations. These devices are the so called field programmable gate arrays (FPGA). It has also been shown that a significant acceleration of the computation time can be achieved by implementing the FDTD code on a graphics processor unit (GPU). These GPU's are basically mass produced, consumer graphics cards found on ordinary PC's. More information about these two methods to accelerate the FDTD computations can be found in the book by Allen Taflove and Susan C. Hagness, "Computational Electrodynamics The Finite-Difference Time-Domain Method; $3^{rd}$ edition", Artech House, Boston, 2005. In this invention regarding the system design of the processing units for the measurement data the hardware constituting the computational resources are constructed using said GPU/FPGA devices. For both this type of FDTD accelerators, GPU/FPGA, the main control of the computational code is maintained by the PC or equivalent. The computer then communicates with the FDTD accelerator to put the FDTD core in place and initiate the simulations. Results are then read back to the computer for different kinds of post processing. See FIG. 3 for a sketch of the system design with the FDTD accelerator in place. It has also been suggested that a combination of GPU and FPGA can be utilized to accelerate the computations since certain parts of the FDTD code can be made to run more efficiently on one device than on the other. It is estimated that an acceleration of about 10:1 can be achieved by using this type of accelerators compared to running a fully optimized FDTD code on an ordinary top of the line PC. Due to the parallel nature of the FDTD simulations required, as discussed above, it is an important part of this invention the utilization several FDTD accelerators in the image reconstruction hardware. The most efficient speed up of the computations is obtained when at least one FDTD accelerator for each transmitting antenna is used. For even better speed up one can also make use of several accelerators for each transmitting antenna. In that case the computational domain is divided between the different accelerator units. When increasing the number of accelerators the speed up will eventually saturate due to the increase of communication between the different units and there will be no or very little benefit of adding more accelerators.

The invention claimed is:

1. A system for non-invasively examination of internal structures of an object by producing dielectric images utilizing reflection and transmission measurements using microwave radiation, comprising:
    an antenna array surrounding a region of interest for the examination,
    a microwave transceiver for measuring reflected and transmitted electromagnetic fields as an electromagnetic pulse, and
    a computational module for receiving detected radiation and for processing data based on said detected radiation, said computational module further being configured to execute a reconstruction procedure utilized to compute an image of a dielectric profile based on permittivity and conductivity properties of tissue under detection,
    wherein the reconstruction procedure comprises an iterative computation series performed using at least some frequencies of the electromagnetic pulse, wherein during each iteration computation i) using a same set, or a different set, of frequencies of the electromagnetic pulse as used in a previously iteration computation, a current gradient is calculated at image points, ii) a reconstructed image from a previous iteration is updated to form updated image data that approaches a final image of tissues expected to be found in the image, wherein the reconstructed image from the previous iteration is updated by assigning an a priori dielectric value to the image points where the current gradient value is above a threshold value, the a priori dielectric value assigned to the updated image points being used in a next iteration computation, wherein the iterative computation series ends when a cost functional based on the permittivity and conductivity properties of the tissue is minimize, the cost functional containing a difference between measured image data and updated image data.

2. The system according to claim 1, being arranged to produce dielectric images of internal biological tissue and structures.

3. The system according to claim 1, being arranged for detecting breast cancer tumors or for detecting other forms of cancer or other anatomical information.

4. The system according to claim 1, wherein said antenna array is mounted in a supporting structure designed as a bra.

5. The system according to claim 1, wherein said antenna array consists of one or several of patch antennas, dipole antennas or monopoles.

6. The system according to claim 1, wherein the antenna array is mounted in fixed positions and with fixed orientations in an antenna array.

7. The system according to claim 1, wherein position and orientation of said antenna array is adjustable.

8. The system according to claim 1, wherein for each imaging occasion the positions and orientations of each antenna is determined relative to each other utilizing microwave transmission measurements between the antennas.

9. The system according to claim 1, comprising external antennas with known positions such that the antennas utilized for the imaging can be positioned relative to the external antennas.

10. The system according to claim 1, comprising lasers or mechanical devices for positioning the antennas.

11. The system according to claim 1, wherein microwave measurements are made at a number of frequencies between a minimum and maximum frequency and more specially the frequency range utilized is within the range 100 MHz to 3 GHz or more.

12. The system according to claim 1, based on time-domain modeling of the electromagnetic imaging system.

13. The system according to claim 1, wherein the typical dielectric properties of tissues are specified as an interval containing physical properties of the tissue.

14. A method for non-invasively examination of internal structures of an object by producing dielectric images utilizing reflection and transmission measurements using microwave radiation, comprising:
- a first step of an antenna array providing frequencies optimized for imaging an overall structure and properties of the object, and
- a second step of a processor determining a frequency content of an electromagnetic pulse optimized to image objects of a target size to thereby improve the resolution of the object structure as to the target size objects, the determination of the frequency content comprising an iterative computation series performed using at least some frequencies of the electromagnetic pulse, wherein during each iteration computation i) a current gradient is calculated at image points, ii) a reconstructed image from a previous iteration is updated to form an updated image data that approaches a final image of tissues expected to be found in the image, wherein the reconstructed image from the previous iteration is updated by assigning an a priori dielectric value to the image points where the current gradient value is above a threshold value, the a priori dielectric value assigned to the updated image points being used in a next iteration computation, wherein the iterative computation series ends when a cost functional based on the permittivity and conductivity properties of the tissue is minimize, the cost functional containing a difference between measured image data and updated image data.

15. The method according to claim 14, further comprising reconstructing at least parts of constitutive dielectric tensor relating an E-field and D-field with the permittivity tensor according to $$\begin{bmatrix} D_x \\ D_y \\ D_z \end{bmatrix} = \begin{bmatrix} \varepsilon_{11} & \varepsilon_{12} & \varepsilon_{13} \\ \varepsilon_{21} & \varepsilon_{22} & \varepsilon_{22} \\ \varepsilon_{31} & \varepsilon_{32} & \varepsilon_{33} \end{bmatrix} \begin{bmatrix} E_x \\ E_y \\ E_z \end{bmatrix}$$

wherein dielectric parameters modeled as an isotropic constant according to the constitutive relations, D=∈E, J=σE.

16. The method according to claim 15, wherein the dielectric tensors are diagonalised in order to find the principal directions of the tissue.

17. The method according to claim 16, wherein principal directions of the tissues are utilized for the purpose of identifying the different tissues.

18. The method according to claim 14, further comprising reconstructing at least parts of constitutive dielectric tensor relating an E-field and J-field with the permittivity tensor according to $$\begin{bmatrix} J_x \\ J_y \\ J_z \end{bmatrix} = \begin{bmatrix} \sigma_{11} & \sigma_{12} & \sigma_{13} \\ \sigma_{21} & \sigma_{22} & \sigma_{22} \\ \sigma_{31} & \sigma_{32} & \sigma_{33} \end{bmatrix} \begin{bmatrix} E_x \\ E_y \\ E_z \end{bmatrix}$$

wherein dielectric parameters modeled as an isotropic constant according to the constitutive relations, D=∈E, J=σE.

19. The method according to claim 18, wherein the dielectric tensors are diagonalised in order to find the principal directions of the tissue.

20. The method according to claim 19, wherein principal directions of the tissues are utilized for the purpose of identifying the different tissues.

21. A method for non-invasively examination of internal structures of an object by producing dielectric images utilizing reflection and transmission measurements using microwave radiation, the method comprising the steps of:
- locating an antenna array to surround a region of interest for the examination,
- a microwave transceiver measuring reflected and transmitted electromagnetic fields at the region of interest as an electromagnetic pulse,
- a. a processor using the measured reflected and transmitted electromagnetic fields to create Finite-Difference Time-Domain (FDTD) simulations of an imaging system,
- b. the processor executing dual Finite-Difference Time-Domain (FDTD) simulations, wherein a driving source is the residual between the forwarded Finite-Difference Time-Domain (FDTD) simulations and the corresponding measurements,
- c. the processor executing a reconstruction procedure comprising an iterative computation series performed using at least some frequencies of the electromagnetic pulse, wherein during each iteration computation i) a current gradient is calculated at image points, ii) a reconstructed image from a previous iteration is updated to form updated image data that approaches a final image of tissues expected to be found in the image,
- wherein the reconstructed image from the previous iteration is updated by assigning an a priori dielectric value to the image points where the current gradient value is above an optimized threshold value, the a priori dielectric value assigned to the updated image points being used in a next iteration computation,
- wherein the gradients are calculated from the forward and the dual Finite-Difference Time-Domain (FDTD) simulations,
- wherein the processor makes a line search where a location of the optimized threshold level in the gradient is determined, and
- wherein the processor further uses the computing gradients in a search process to find if the already found objects are located in the correct position or if they should be moved, wherein the line search involves plural Finite-Difference Time-Domain (FDTD) simulations where a cost functional is evaluated and bases on these evaluations the minimum point of the cost functional is estimated, and
- d. the processor updating object and starting the process from step b, and iterating the procedure until the reconstruction process has converged,
- wherein the cost functional is based on the permittivity and conductivity properties of the tissue, and the cost functional contains a difference between measured image data and updated image data.

22. A system for non-invasively examination of internal structures of an object by producing dielectric images utilizing reflection and transmission measurements using microwave radiation, comprising:
- an antenna array surrounding a region of interest for the examination,
- a microwave transceiver for measuring reflected and transmitted electromagnetic fields as an electromagnetic pulse,
- a computational module for receiving detected radiation and for processing data based on said detected radiation, said computational module further being operatively arranged to execute a reconstruction procedure utilized to compute an image of the dielectric profile under detection, the dielectric profile based on permittivity and conductivity properties of tissue, the reconstruction procedure comprising an iterative computation series performed using at least some frequencies of the electromagnetic pulse, wherein during each iteration computation i) a current gradient is calculated at image points, ii) a reconstructed image from a previous iteration is updated to form updated image data that approaches a final image of tissues expected to be found in the image, wherein the reconstructed image from the previous iteration is updated by assigning an a priori dielectric value to the image points where the current gradient value is above a threshold value, the a priori dielectric value assigned to the updated image points being used in a next iteration computation, wherein the iterative computation series ends when a cost functional based on the permittivity and conductivity properties of the tissue is minimize, the cost functional containing a difference between measured image data and updated image data a field programmable gate arrays (FPGA), and a graphics processor unit (GPU) implementing Finite-Difference Time-Domain (FDTD) code thereon.

* * * * *

UNITED STATES PATENT AND TRADEMARK OFFICE
CERTIFICATE OF CORRECTION

PATENT NO. : 8,724,864 B2  Page 1 of 1
APPLICATION NO. : 12/302055
DATED : May 13, 2014
INVENTOR(S) : Persson et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1009 days.

Signed and Sealed this
Twenty-ninth Day of September, 2015

Michelle K. Lee
*Director of the United States Patent and Trademark Office*